United States Patent
Devoto

(10) Patent No.: US 11,107,569 B1
(45) Date of Patent: Aug. 31, 2021

(54) REWARD-BASED HEALTH ACTIVITY MOBILE APPLICATION AND SYSTEM

(71) Applicant: LVLFI, Ltd, London (GB)

(72) Inventor: Alexander William Gregory Devoto, London (GB)

(73) Assignee: LVLFI, Ltd, London (GB)

( * ) Notice: Subject to any disclaimer, the term of this patent is extended or adjusted under 35 U.S.C. 154(b) by 0 days.

(21) Appl. No.: 16/838,669

(22) Filed: Apr. 2, 2020

(51) Int. Cl.
*G16H 20/30* (2018.01)
*H04L 29/08* (2006.01)
*G06Q 40/08* (2012.01)
*G16H 40/63* (2018.01)
*G06F 1/16* (2006.01)
*G16H 40/67* (2018.01)

(52) U.S. Cl.
CPC ............ *G16H 20/30* (2018.01); *G06F 1/163* (2013.01); *G06Q 40/08* (2013.01); *G16H 40/63* (2018.01); *G16H 40/67* (2018.01); *H04L 67/22* (2013.01)

(58) Field of Classification Search
CPC ........ G16H 20/30; G16H 40/63; G16H 40/67; G06Q 40/08; G06F 1/163; H04L 67/22
See application file for complete search history.

(56) References Cited

U.S. PATENT DOCUMENTS

| | | |
|---|---|---|
| 5,142,358 A | 8/1992 | Jason |
| 5,456,648 A | 10/1995 | Edinburg et al. |
| 5,730,654 A | 3/1998 | Brown |
| 6,302,789 B2 | 10/2001 | Harada et al. |
| 8,894,547 B2 | 11/2014 | Bruno |
| 9,786,127 B2 | 10/2017 | Marshall et al. |
| 10,279,247 B2 | 5/2019 | Kiani |
| 10,493,364 B2 | 12/2019 | Dugan |
| 2010/0125028 A1 | 5/2010 | Heppert |
| 2012/0041767 A1 | 2/2012 | Hoffman et al. |

(Continued)

OTHER PUBLICATIONS

Charanjeet Singh, "Snapchat Streak Lost? Here Is How To Restore It", fossbytes.com, Published: Mar. 25, 2020, URL: < https://fossbytes.com/snapchat-streak-lost-here-is-how-to-restore-it/ >, Accessed: May 25, 2020 (Year: 2020).*

(Continued)

*Primary Examiner* — Victoria P Augustine
*Assistant Examiner* — Chad A Newton
(74) *Attorney, Agent, or Firm* — Loomis Law Firm; Mikhail Murshak

(57) ABSTRACT

A reward-based health activity and exercise mobile application that utilizes an activity monitoring device to track activity data and transmits the data to a mobile device to generate virtual lottery tickets. A mobile application on the mobile device analyzes the activity data and determines if the user has completed the daily health-related goals. If the user completes the daily goal, the user is awarded a virtual lottery ticket reward that can be used for raffles of real prizes. If the user completes exercise and non-exercise goals for consecutive days, the user is awarded with additional streak bonus rewards on an escalating basis. The mobile application can be connected to a communication network whereby users can join teams and other communities to track activity data and compete against other users. A streak saver feature can be provided to allow a user to maintain a streak by performing a task.

20 Claims, 7 Drawing Sheets

(56) References Cited

U.S. PATENT DOCUMENTS

| | | | | |
|---|---|---|---|---|
| 2013/0197679 A1* | 8/2013 | Balakrishnan | ......... | G16H 20/40 |
| | | | | 700/91 |
| 2013/0325501 A1* | 12/2013 | Walker | ...................... | A61J 7/04 |
| | | | | 705/2 |
| 2014/0011571 A1* | 1/2014 | Roper | ................ | G07F 17/3262 |
| | | | | 463/23 |
| 2014/0156292 A1* | 6/2014 | Kozicki | ................. | G06Q 50/22 |
| | | | | 705/2 |
| 2014/0180454 A1* | 6/2014 | Weast | ................ | A63B 71/0622 |
| | | | | 700/91 |
| 2014/0244009 A1* | 8/2014 | Mestas | ................... | G16H 40/63 |
| | | | | 700/91 |
| 2014/0379106 A1* | 12/2014 | Weast | ................ | A63B 24/0059 |
| | | | | 700/91 |
| 2015/0281384 A1* | 10/2015 | Gunnarsson | ........... | G16H 20/60 |
| | | | | 709/204 |
| 2016/0213924 A1* | 7/2016 | Coleman | ............ | A61N 1/36031 |

OTHER PUBLICATIONS

Pattiandfoster (pattiandfoster, "Question: Q: Is There a Way to Restore the Move Streak Achievement after the Recent Watch Update?" Is There a Way to Restore the Move Streak . . . —Apple Community, Published: Apr. 12, 2016, URL: < https://discussions. apple.com/thread/7523902 >, Accessed: Apr. 19, 2020) (Year: 2016).*
Sweatcoin, Mobile application which pays users a digital currency based on their daily steps, Jan. 18, 2018, article on Mobihleathnews. com, 15 pages, internet.

\* cited by examiner

REWARD-BASED HEALTH ACTIVITY MOBILE APPLICATION AND SYSTEM

TECHNICAL FIELD

The present disclosure relates generally to a system and method in the field of mobile applications and digital medium, more specifically in the field of health and physical activity.

DESCRIPTION OF RELATED ART

Exercise and physical activity are becoming an increased focus in today's society. When coupled with a healthy and nutritious diet, exercise can form the building block of a healthy lifestyle. While most, if not all, people understand the importance of exercise, many have difficulty finding the motivation required to start and maintain a stimulating fitness program catered to that person's needs. Weight loss is often the driving factor for engaging in physical activity and exercise programs. However, often the motivation to continue with a given exercise program is lost once that person achieves their weight loss target. Regular exercise helps combat health conditions and diseases, promotes better sleep, improves muscle strength, boosts endurance, improves libido and boosts the body's energy levels. Improved health can reduce costs to the individual directly, their employer, and society overall.

Studies have shown that a person should have at least 150 minutes of moderate exercise per week, or 30 minutes per day. On average, 30 minutes of walking is equivalent to taking 4,000 steps. Often, a target for daily steps is 10,000 steps per day. While this target of 10,000 steps will not automatically lead to immediate weight loss or a healthy lifestyle, it does provide a person with extra motivation to get up and be active. Incorporating high-intensity exercise with the target steps can be a significant goal to achieve improved physical condition. Attempts have been made at creating rewards to motivate and incentivize individuals to continue their exercise regimen and achieve and maintain healthy lifestyles. Some have created virtual currency or other incentives to encourage individuals to exercise.

U.S. Pat. No. 8,894,547 to Bruno discloses power generation via fitness machines. Specifically, this patent relates to a system and method for generating power via the use and operation of fitness machines. Further, embodiments are configured to utilize characteristics and/or data points associated with the use and operation of such fitness machines to calculate and reward users with one or more virtual currencies.

U.S. Pat. No. 10,279,247 to Kiani discloses an avatar-incentive healthcare therapy system with a physiological monitor for generating a physiological parameter indicative of physical health. An academic test for generating a test score is indicative of mental acuity. The avatar has outward characteristics and game play capabilities proportional to the physiological health and the mental acuity so as to incentivize improved physical health and academic performance.

U.S. Pat. No. 5,142,358 to Jason discloses an earn per view device affording variable viewing on a television as a reward for accomplishment of a positive task on an exercise machine, computer, electronic glove or other associated device. A tabulation and accumulation device tabulates and accumulates the amount of positive task performed on the associated positive task device. A control device for controlling the access to viewing on the associated video device in electrical communication with the tabulation and accumulation device. The control device may be activated by the user to afford viewing on the television in proportion to the quantity of positive task accumulated by the tabulation and accumulation device.

U.S. Pat. No. 5,456,648 to Edinburg et al. discloses a method and apparatus for exercise in which a preselected work is inputted to an exercise machine that is associated with an award-granting switch triggers a reward. The input can be a particular rate of work as measured by rotational speed or linear motion or a summation of the time during which a threshold level of work was exceeded. The reward can be turning on a TV or like electrical apparatus or it can be a change in the exercise machine and regime. An exercise machine incorporating the award-granting switch is disclosed in which the reward is a change in the angle to horizontal at which the exercise is performed. This change can make the exercise harder or easier depending on the exercise protocol desired.

U.S. Published App. No. 2012/0041767 to Hoffman et al. discloses the monitoring and tracking by an athletic monitoring and tracking device and service of user activity including both athletic activity (e.g., running, walking, etc.) and non-athletic activity (shopping, reading articles, etc.). The user activity may be used to award a user with an amount of virtual currency to encourage the user to continue various activities. Users may use the virtual currency to purchase or otherwise acquire various products, services, discounts and the like. A user may track an amount currency earned and/or needed relative to an amount required to acquire a desired product or service. Additionally, or alternatively, a visual appearance of a user device (e.g., a watch or athletic activity band) may change based on the user's activity level, an amount of virtual currency earned and the like.

U.S. Pat. No. 6,302,789 to Harada et al. discloses a pedometer with game mode which can be used as a game by a child to get some exercise such as walking and/or running without reluctance. When a vibration is detected by a vibration detector, the count values of a step-number counter and an integrating counter are incremented, and thereby a display state of a character displayed on an LCD is varied based on the count values of step-number counter and/or the integrating counter.

U.S. Pat. No. 10,493,364 to Dugan discloses an application that is adapted to execute on at least a first mobile device. The application is adapted to (a) track information regarding a user of the mobile device; (b) create an avatar based on the tracked information; and (c) employ the avatar to provide pre-emptive warnings to assist in avoidance of unwanted behavior by the user.

U.S. Pat. No. 5,730,654 to Brown discloses a multi-player video game for health education encourages inter-player communication about a health condition by correlating the players' progress. Each player manages the health of a game construct such as a game character or body region. Correlating the player's game progress is achieved through: common scoring; conditioning a player's passage to higher levels on the health management success of all players; and common game resources, including game resources representing devices or supplies used in the care of the health condition. Applications include children' health education related to diseases such as diabetes and asthma, as well as health habits such as dental hygiene, and tobacco, alcohol and drug use.

U.S. Published App. No. 2010/0125028 to Heppert discloses a physical activity reward system and method which rewards a person performing physical activity with a reward, such as use of an appliance such a TV viewing time. The system includes a physical activity monitor capable of generating activity information proportionate to the amount of exertion or work done. The system may be used to record and keep track of the reward points or information. The system may further control the supply of electricity to an appliance through an electrical control module. The electrical control module may be interposed between a source of household electrical current and an electrical appliance such as a TV set.

These examples are representative of physical activity and exercise programs and reward-based incentives for said physical activity and exercise. However, none of the above, taken either alone or in combination achieve the benefits or describe the features of the present disclosure.

SUMMARY

The present disclosure provides for a reward-based mobile application or other digital medium system for the monitoring and tracking of health-related tasks of a user and providing reward-based incentives. The mobile application system is downloaded and installed on a mobile device. In an example, the mobile device can be a smart phone, tablet, or other computing device. The mobile device or other computing device synchronizes and communicates with an activity monitoring device. The activity monitoring device can be a wearable computing device such as a smart watch or wearable pedometer, or other fitness tracking dedicated device or application hosted on the user's mobile phone. The activity monitoring device measures and calculates the number of steps taken by the user and transmits that data to the mobile device. The mobile application then gathers the data received from the mobile device, analyzes the data, and determines the number of steps taken. The data is then displayed on a hub represented by a graphical user interface on the mobile application where the user can readily determine the activity data such as the number steps taken in a given period. The hub then compares the activity data to various pre-determined goals. If the user achieves the various goals set forth in a given period, then the user is rewarded with a virtually generated reward. In an example, the virtually generated reward is a virtual lottery ticket whereby the user can use the lottery ticket to enter a raffle for a chance to win assorted prizes.

The various goals can be any physical activity goal set for the user. In an example, the user can be rewarded for completing a pre-determined number of steps in a day. In another example, the user can be rewarded for checking in to the mobile application. In yet another example, the user can be rewarded for reading an informational article, perhaps related to health and fitness or insurance, and answering questions related to the article. The article can be related to any field, including but not limited to exercise, diet, nutrition, and health and wellness. The user is incentivized to achieve goals in consecutive days, also called "streaks." By completing streaks for the various goals, the user is rewarded with additional virtual lottery tickets at an proportional rate compared to the length of the streak. In a further example, if a user fails to achieve one of the goals, the user can complete a "streak-saver" where the user completes additional steps in the next period in order to maintain the current streak for the goal. Upon a failure of the goal, the user will be prompted to choose to utilize the streak-saver. If the user chooses to use the streak-saver, the user can complete additional tasks the following day, and if completed, the streak will be "revived" and the streak rewards continued.

The present disclosure also provides for a community network system where users can share their activity data with other users. The mobile application communicates with a communication network through the internet. The communication network connects with other users' mobile applications who are also sharing their activity data. The users can view other users' activity data, providing additional incentive and motivation to increase exercise and physical activity output. Users can create teams and invite friends, family, and/or coworkers to join a team. Once a part of a team, the users can view the total number of steps accrued and goals achieved of the other users. The application further displays a team leaderboard, which ranks the users based on the activity data such as the highest steps achieved that day.

The present disclosure further provides for a system for employers to incentivize employees to engage in wellness and exercise programs. The employers can create a team and allow and/or require the employees to join that team. The employer can then monitor the employees' progress and daily exercise regimes and programs. The employer can then reward, incentivize, or offer discounts and/or rebates on insurance premiums for participation and success in the wellness program through the mobile application.

For purposes of summarizing the disclosure, certain aspects, advantages, and novel features of the disclosure have been described herein. It is to be understood that not necessarily all such advantages may be achieved in accordance with any one particular embodiment of the disclosure. Thus, the disclosure may be embodied or carried out in a manner that achieves or optimizes one advantage or group of advantages as taught herein without necessarily achieving other advantages as may be taught or suggested herein. The features of the disclosure which are believed to be novel are particularly pointed out and distinctly claimed in the concluding portion of the specification. These and other features, aspects, and advantages of the present disclosure will become better understood with reference to the following drawings and detailed description.

BRIEF DESCRIPTION OF THE DRAWINGS

The figures which accompany the written portion of this specification illustrate example embodiments and methods of use for the present disclosure.

The various embodiments of the present disclosure will hereinafter be described in conjunction with the appended drawings, wherein like designations denote like elements.

DETAILED DESCRIPTION

Figure 1:
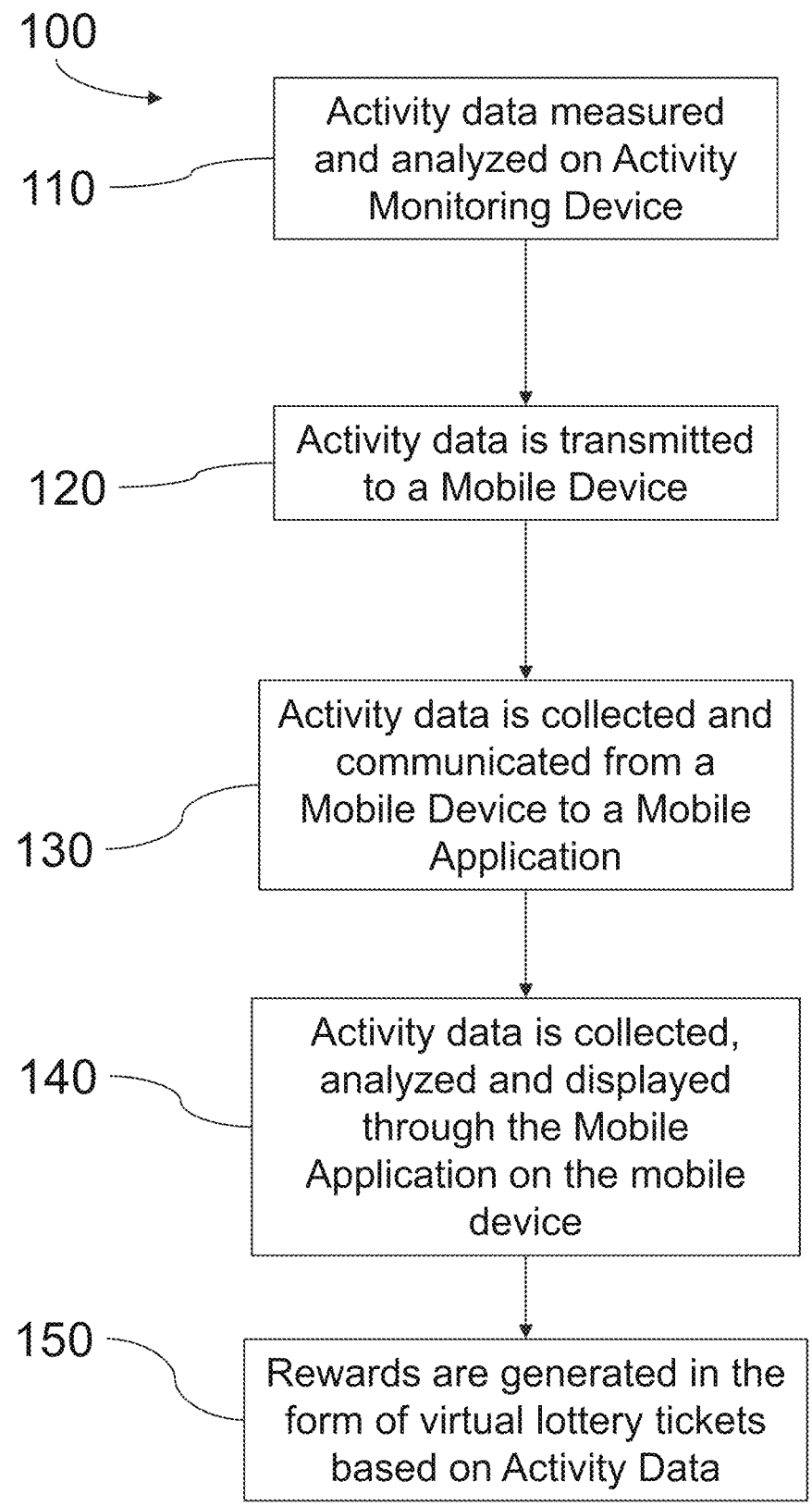
FIG. 1 illustrate a schematic flow diagram related to collecting of activity data to generating rewards.

As discussed above, embodiments of the present disclosure relate to a system and method for a reward-based mobile application and other digital medium, more specifically in the field of health and physical activity.

Health related tasks and physical activity can be essential to an individual's everyday routine in order to maintain a healthy lifestyle. Regular exercise is not only important for weight loss, but also for preventing disease and illness, reducing stress, improving libido, and increasing energy levels. Often times, motivation to regularly exercise is lost for a variety of different reasons. Regaining that motivation and maintaining it has proven to be a difficult challenge in the healthcare and fitness industries alike. The present disclosure provides for a system for a mobile application and other digital medium that rewards users for their completion of health-related tasks performed on a continuous basis. Users are rewarded for completing various physical activity achievements and/or health-related activity in a given day. The reward is provided in a form of virtually generated rewards that can be exchanged for virtual currency for virtual "lottery", "gambling" or "games of chance" for winning "real" prizes and gifts. Moreover, the user can be connected to a community, for example, a group of coworkers or an entire enterprise associated with the user's place of employment. This can have the added benefits associated with healthy competition and peer pressure to achieve common goals. In another example, team competitions can be established that provides additional motivation for completing tasks together.

Referring to the drawings, FIGS. 1-4 provide exemplary schematic diagrams illustrating the system and method of the present disclosure. In these examples, physical activity data is collected, analyzed, and rewards are generated. The overarching goal is to motivate users to reach health-related goals and reward the users for the achievements of those goals. Moreover, this system is effective in creating stickiness to motivate users to repeat the tasks on a daily basis and increases participation. This can be achieved through the use of a mobile application. In this example, the mobile application is installed on a mobile device or tablet. The user can input user specific information like biographical and bodily information. This can be used as a baseline for improvement and/or to better ascertain the user's level of physical fitness. In another example, the user can then be measured through the use of an activity monitoring device. In an example, the activity monitoring device is a wearable computing device such as a smart watch, a wearable pedometer, or other fitness tracking dedicated device or application hosted on the user's mobile phone. In a further example, the activity monitoring device is a smart mobile device that has pedometer functionality.

Referring specifically to FIG. 1, system 100 is provided that is associated with the present disclosure. In this example, at box 110, an activity monitoring device measures activity data of the user for a portion of or the entire day. This can include activity data that includes but is not limited to, steps taken, heart rate, calories burned, exercise time, and combinations thereof. Once the user's activity data is measured, collected and analyzed (box 110) by the activity monitoring device, the data is transmitted to the user's mobile device in box 120. In an example, the activity data collected from the activity monitoring device is transmitted to the mobile device through short-range wireless communications such as BLUETOOTH.

When the activity data is transmitted to the mobile device or tablet, a mobile application collects and reads that data at box 130. The mobile application then analyzes the activity data and displays the information for the user to see at box 140. Within the mobile application, it is determined whether the user has achieved a health-related goal for that day or preset period of time. This can include satisfying a preset criterion, like walking a preset number of steps or walking for a given period of time. In an example, an exercise goal is to achieve 5,000 steps in a day. In a further example, an exercise goal can be to achieve 10,000 steps in a 16-hour period. In yet another example, a non-exercise goal is to check-in to the mobile application that day or read health related content provided within the mobile application followed by, perhaps answering questions related to the article. In a further example, a non-exercise goal is to read a selected article on the mobile application in a day. The selected article can be an article ranging in topics from health and wellness, exercise, diet, nutrition, insurance, and physical fitness, among other topics. If the user has achieved one of the exercise or non-exercise goals, then the mobile application awards the user with a virtual reward for achieving the goal via box 150. In an example, the virtual reward is a virtual lottery ticket that the user can submit for a chance to win real prizes and gifts. The more lottery tickets the user collects, the greater their odds for winning better prizes.

Figure 2:
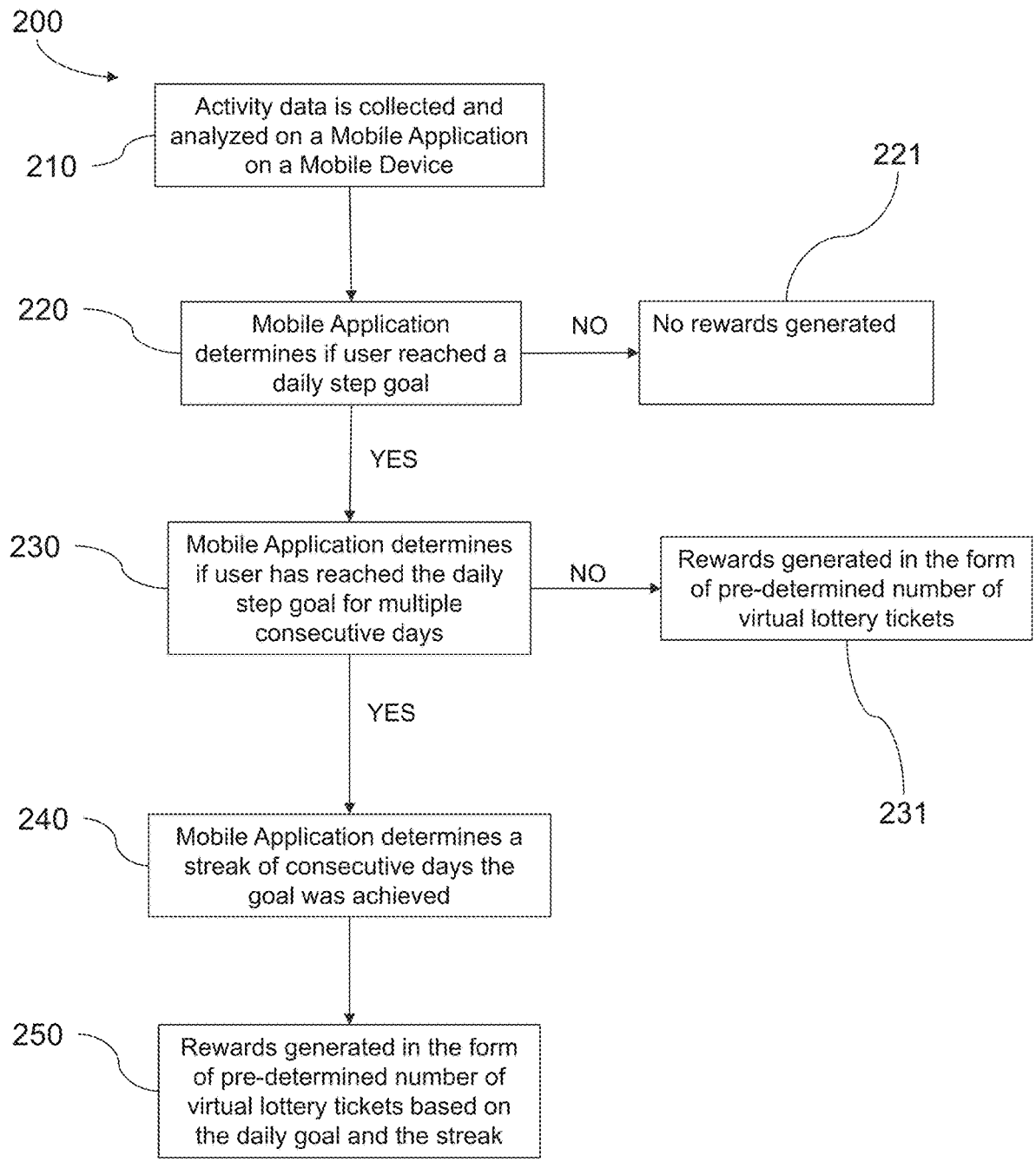
FIG. 2 illustrates a schematic flow diagram related to a reward system for a daily steps goal including the reward system for streaks of the daily steps goal.
Figure 3:
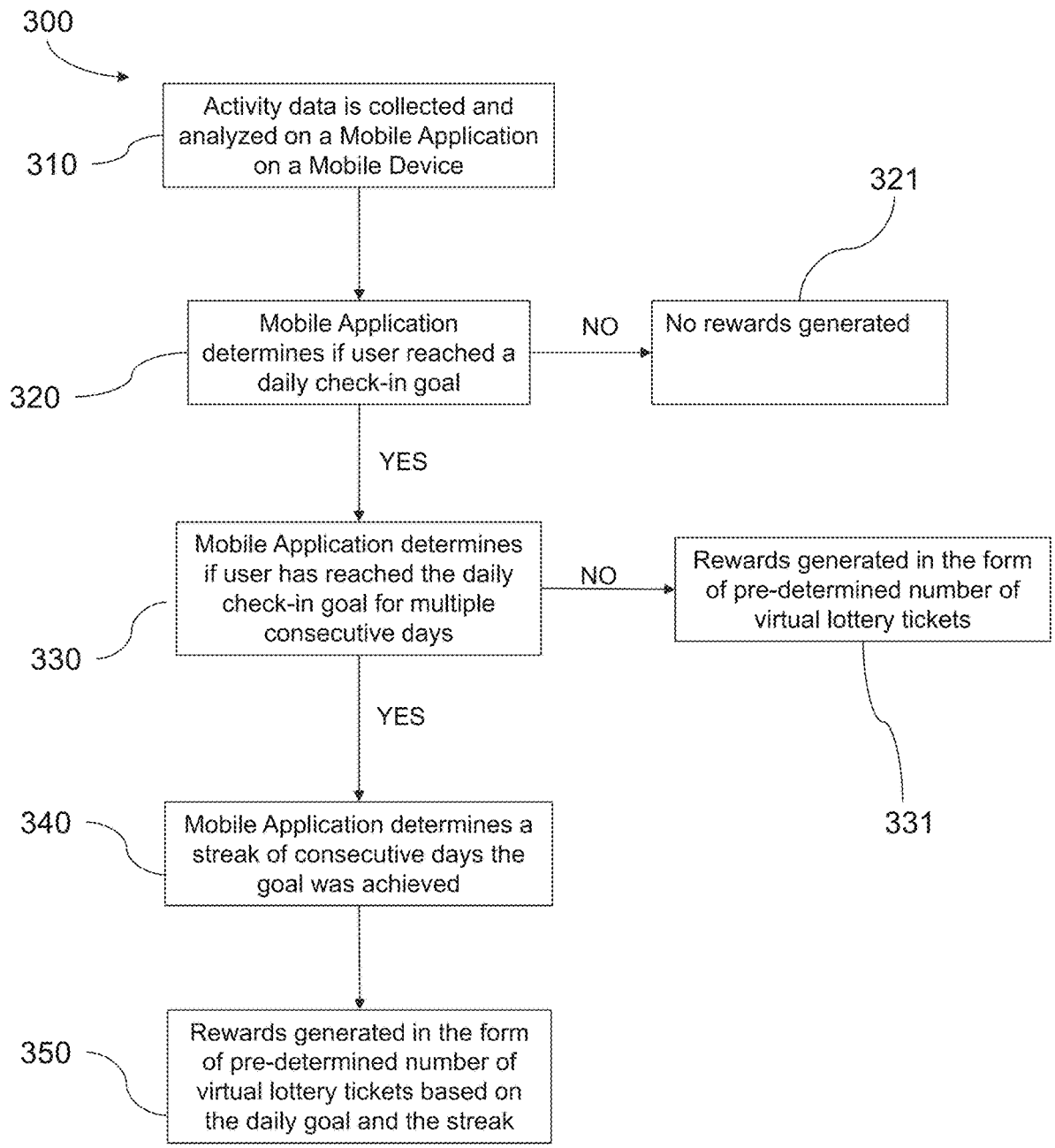
FIG. 3 illustrates a schematic flow diagram related to a reward system for a daily check-in goal including a reward system for streaks of the daily check-in goal.
Figure 4:
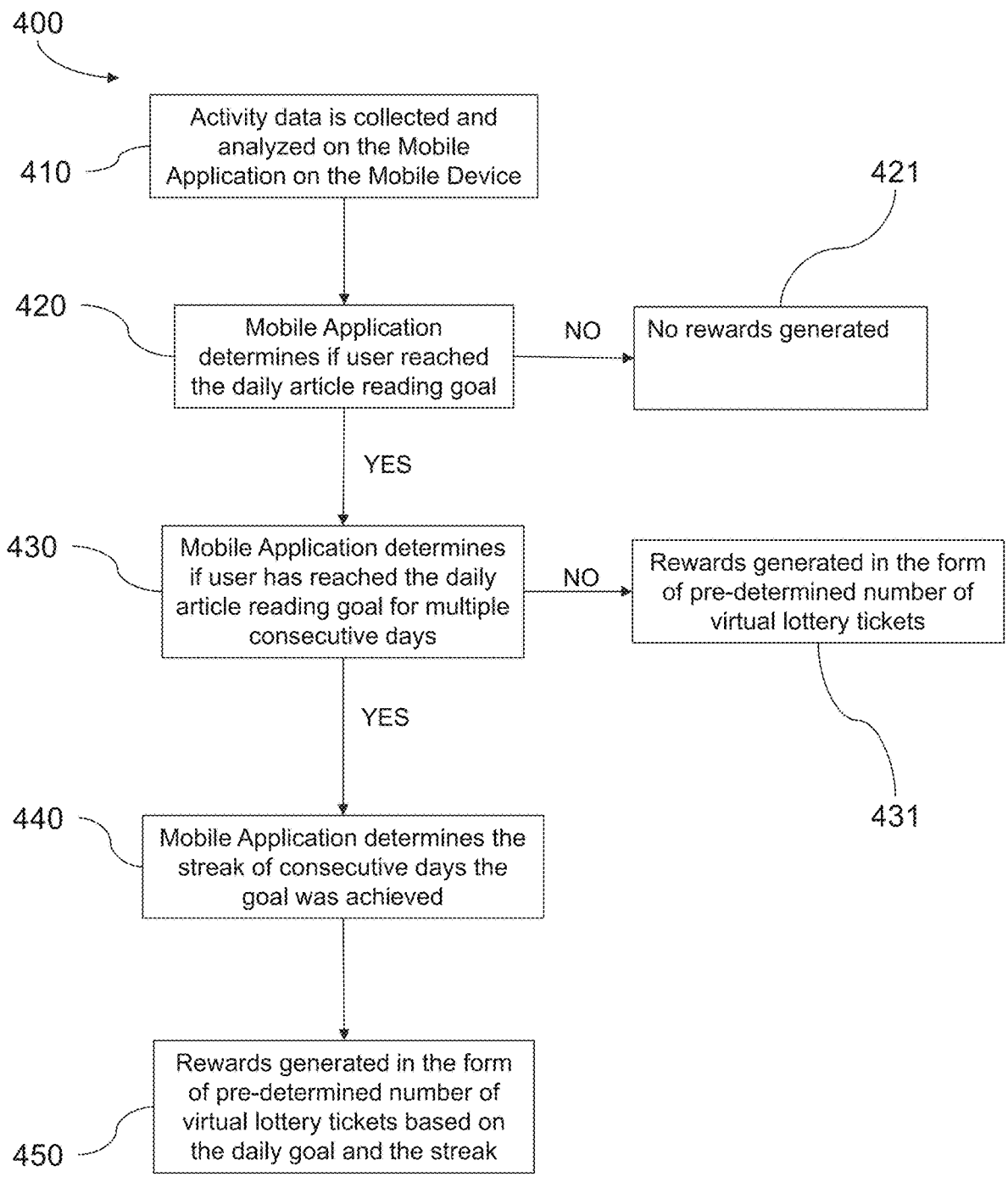
FIG. 4 illustrates a schematic flow diagram related to a reward system for a daily article reading goal including a reward system for streaks of the daily article reading goal.

Referring to FIGS. 2-4, the user is incentivized to complete the exercise and non-exercise goals for consecutive days in order to achieve a "streak." System 200 provides for a process of obtaining rewards that is associated with the present disclosure. The activity data generated from the activity monitoring device is transmitted to and collected by the mobile device at box 210. The mobile application analyzes the activity data and determines if the user has reached the health-related goal at box 220. In this example, the goal is the daily step goal. If the user has not completed any goals, then the user is not given any rewards via box 221. If, however, the user has achieved a health-related goal, the mobile application will determine if the user has completed that goal for a number of consecutive days or other set period of time at box 230. If the user has only completed that goal for only that day, then the user is granted the daily reward at box 231. If the user has completed the goal for consecutive days, then the user is rewarded both the daily reward and the streak bonus reward, which is based on the consecutive number of days of the streak via box 250.

FIGS. 3-4 embody a similar system to system 200. FIG. 3 details a representation of system 300 which provides for a streak-based system by rewarding a daily check-in goal shown in box 320. FIG. 4 details a representation of system 300 which provides for a streak-based system by rewarding a daily article reading goal shown in box 420. In a further example, if a user fails to achieve a goal for the day, the user can complete a "streak-saver" where the user completes additional steps in the next period in order to maintain the current streak for the goal. For example, if the user has an 11 day 5,000-step streak, but only achieves 4,500 steps on day 12, then the user can complete a streak-saver by completing 7,500 steps on day 13. Once the user completes the streak-saver on day 13, the streak continues at 13 days, rather than restarting at zero on day 12.

In the present disclosure, the virtual currency such as virtual "lottery", "gambling" or "games of chance" tickets (hereinafter called lottery tickets) can have various levels of worth. In an example, a bronze lottery ticket is less valuable than a silver lottery ticket, which is less valuable than a gold lottery ticket, which is less valuable than a black lottery ticket. In an example, the bronze and silver lottery tickets can be earned by completing streaks for exercise or health related goals. In a further example, the gold lottery tickets can be earned by completion of the daily health-related goals. In yet a further example. the user can have the option to trade in bronze lottery tickets and silver lottery tickets for gold lottery tickets. The gold lottery ticket can then be submitted to enter raffles for a chance to win prizes and gifts. The more gold lottery tickets the user collects, the greater their odds for winning prizes. The black lottery tickets can be earned by exceeding an increased step goal. The black lottery tickets can then be submitted to enter a VIP raffle with a chance to win more exclusive prizes. Although these examples use color as a basis for lottery tickets, any effective indicia can satisfy the difference among lottery ticket differentiation or identity. For example, instead of colors, animal or royalty designations can be used, such as deer, wolf, lion or jester, prince, princess, king, queen levels. In an example, 5-10 bronze tickets can be traded in for a silver ticket and 5-10 silver tickets can be traded in for a gold ticket. In yet another example, 5-10 gold tickets can be traded in for a black ticket. In a further example, 10 bronze tickets can be traded in for 1 gold ticket and 3 silver tickets can be traded in for 1 gold ticket and black tickets cannot be obtained through trade-in. The increase in value of each level of ticket provides additional motivation, gamification and incentives to the user community.

Figure 5:
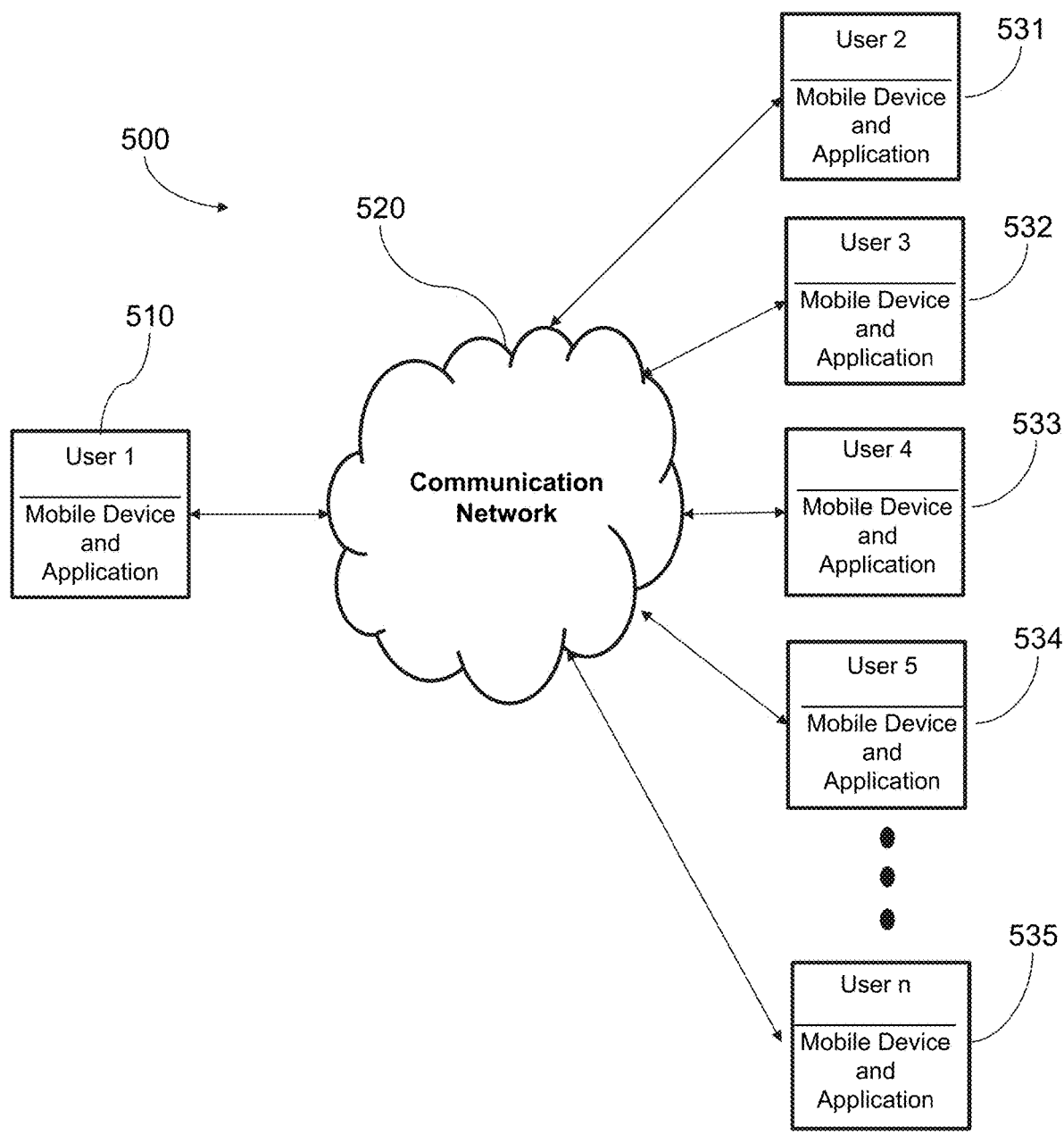
FIG. 5 illustrates a system of communication with one or more users through one or more mobile devices over a communication network.

FIG. 5 provides an exemplary schematic diagram of a network communication system 500 between users of the mobile application, whereby users can share their activity data with other users. Mobile device and mobile application 510 communicate with communication network 520 via a network system such as the internet. The communication network engages with other users' mobile applications whereby there is an exchange of information between the devices, specifically the user's activity data. Specifically, User 1 can connect with User 2 via box 531, User 3 via box 532, User 4 via box 533, and User 5 via box 534 at the same time through the use of the communication network. Such connection further allows Users 2-5 to connect with each other as well as User 1 through the communication network. Further, User 1 can connect with any number of individuals, as represented by User "n" in box 535. Users can view each other's activity data, which provides the user with an additional incentive and motivation to increase exercise and physical activity. In an example, users can create teams and invite friends, family, and/or coworkers to join a team. Once a part of a team, the users within the team can view other user's activity data, such as the total number of steps accrued and goals achieved. In a further example. the mobile application displays the leaderboard for the team, which ranks the users based on with the highest number of steps completed that day.

Network communication system 500 further provides for an incentive program for employers to incentivize employees to engage in wellness and health-related programs. In an example. the employers can create a team that employees can join. The employer can then monitor the employees' progress and daily exercise regimes and programs. The employer can then reward, incentivize, and offer discounts and/or rebates on insurance premiums for participation and success in the wellness program monitored by the mobile application.

Figure 6:
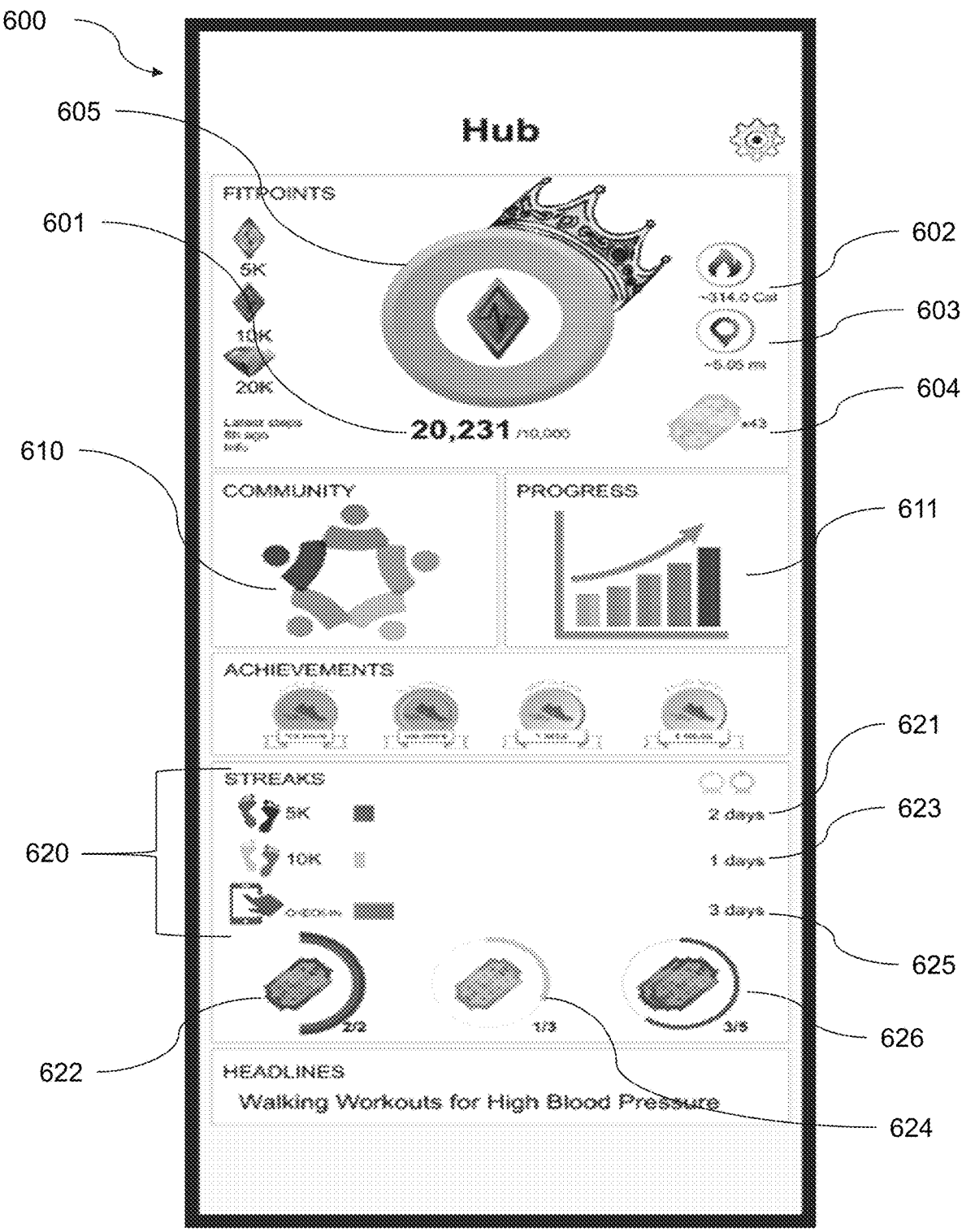
FIG. 6 illustrates a schematic drawing of a graphical user interface of a mobile application on a user's mobile device.

FIG. 6 shows a schematic drawing of the graphical user interface of the mobile application that can be visually displayed on the mobile device. The graphical user interface is displayed on the example of a hub 600. Hub 600 can be a user specific summary that displays the activity data gathered for the day to the user. In this example, a counter 601 displays the number of steps taken in comparison to the step goal of 10,000. The number of calories burned are shown on a counter 602. The number of approximate miles traversed are shown on a counter 603. These features can be modified and customized depending on the goals of a particular user or community. The number of approximate calories and miles can be estimated based on the number of steps taken and optionally related to specific biometric information of the user such as height and weight. In an example, the user can input his or her height, weight, and walking speed to more accurately estimate the calories burned and distance traveled. An icon 604 shows the number of gold tickets earned by the user. A portal 610 takes the user to a community network whereby the user can join teams and view other users' activity data and achievements such as daily steps, total steps, and streaks. A portal 611 takes the user to a "progress" tab which displays archived activity data of the user. In an example, the user can see a weekly report of the steps taken, a monthly report of the steps taken, the longest streaks for the 5,000-step goal and 10,000-step goal, and the lifetime distance traveled based on the total amount of steps taken.

An indicator 620 shows the various icons for the streaks for the exercise and non-exercise goals. In an example, the 5,000-step goal is represented by pink feet, the 10,000-step goal is represented by blue feet, and the check-in goal is represented by a purple hand and mobile device. In a further example, the daily article reading goal is represented by a different icon. A counter 621 displays the number of consecutive days that the user has completed the 5,000-step goal. An icon 622 shows the progress towards receiving the streak bonus reward for the 5,000-step goal. In an example, the streak bonus reward for the 5,000-step goal is a bronze lottery ticket. A counter 623 displays the number of consecutive days that the user has completed the 10,000-step goal. An icon 624 shows the progress towards receiving the streak bonus reward for the 10,000-step goal. In an example, the streak bonus reward for the 10,000-step goal is a silver lottery ticket. A counter 625 displays the number of consecutive days that the user has completed the check-in goal. An icon 626 shows the progress towards receiving the streak bonus reward for the check-in goal. In an example, the streak bonus reward for the check-in goal is two bronze lottery tickets.

Figure 7A:
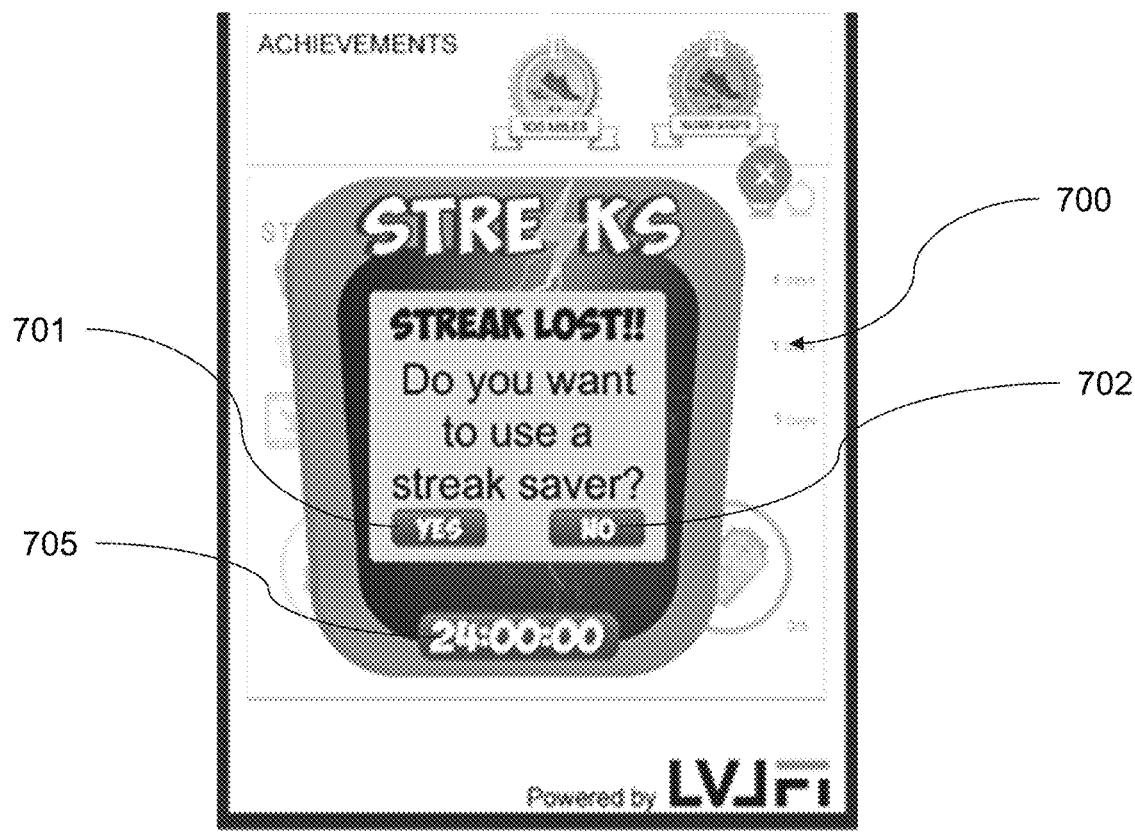
FIGS. 7A-7B illustrate graphical user interfaces of a mobile application with a streak-saver prompt and streak-saver in use, respectively.
Figure 7B:
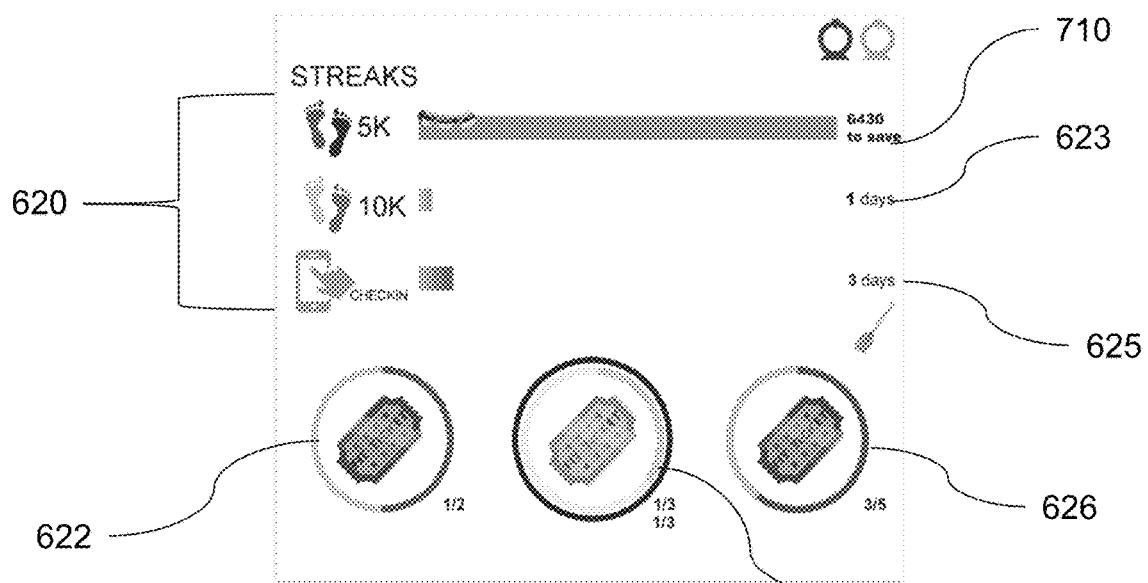

FIGS. 7A-7B show schematic drawings of the graphical user interface of the mobile application of a streak-saver prompt and streak-saver in use, respectively. A streak-saver prompt 700 allows a user to save, or "revive", a lost streak by completing additional tasks the next day. For example, if a user fails to achieve the 5,000-step goal and maintain the streak, the application is configured to prompt the user to choose to utilize a streak-saver 700 to revive the failed streak. If successfully revived, the user's streak will be continued, and additional rewards will be generated for the user. So, if the user fails the 5,000-step goal on day 11, then the user can utilize streak-saver 700 and complete the additional exercise on day 12. If successful, the user's streak will be revived from zero to 12 days. In an example, the additional exercise required to revive a 5,000-step streak is to complete 7,500 steps the next day. In another example, the additional exercise required to revive a 10,000-step streak is to complete 14,000 steps the next day. In yet a further example, the additional exercise required to revive a daily check-in streak is to complete 5,000 steps the next day.

Upon the failure of a goal and loss of a streak, the user is prompted to utilize the streak-saver from the streak-saver 700. If the user decides to use the streak-saver, the user selects button 701. If the user decides not to use the streak-saver, the user selects button 702. The user has the amount of time to revive the streak as indicated in timer 705. In an example, the application is configured to generate one streak-saver every week. If the user opts to revive the streak, icon 710 appears where the respective counter for the appropriate streak would appear on the hub. Icon 710 indicates to the user the number of steps required to revive the streak.

The embodiments of the disclosure described herein are exemplary, and numerous modifications, variations and rearrangements can be readily envisioned to achieve substantially equivalent results, all of which are intended to be embraced within the spirit and scope of the disclosure. Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application.

What is claimed is:

1. A system for a reward-based health program, comprising:
   (a) a mobile device having a visual user interface, a processor, a storage unit configured to store data, and a wireless communication module configured to wirelessly communicate;
   (b) a mobile application provided on the mobile device configured to communicate with a remote online community through the wireless communication module; and
   (c) an activity monitoring device including one or more sensors configured to detect and track physical activity data related to an activity performed by a user including step counts, wherein the activity monitoring device is configured to track the physical activity data through the mobile application;
   wherein the mobile application is configured to collect and store the physical activity data and generate rewards to the user with virtual lottery tickets based on achieving daily goals associated with the physical activity data,
   wherein the virtual lottery tickets are configured to be applied by the user to enter raffles for prizes through the mobile application,
   wherein the visual user interface is configured to display the virtual lottery tickets, progress related to the goals, and the physical activity data; and
   wherein the mobile application is configured to: (i) generate rewards with virtual lottery tickets for streaks associated with achieving the daily goals, (ii) determine a lost streak when a daily goal is not completed on that day, (iii) generate a streak-saver prompt on a next day following the day of the lost streak on the visual user interface to revive the lost streak; and (iv) generate a streak-saver health-related activity task on that next day upon completion of which revives and continues the streak as if the lost streak had not occurred.

2. The system according to claim 1, wherein the activity monitoring device is a wearable computing device including a pedometer and configured to wirelessly communicate with the mobile device.

3. The system according to claim 1, wherein the activity monitoring device is incorporated in the mobile device and comprises a pedometer configured to measure steps taken by the user.

4. The system according to claim 3, wherein the mobile application is configured to generate daily goals in the form of a task related to physical activity and reward the user with virtual lottery tickets for completing the daily goals.

5. The system according to claim 1, wherein the system is configured to reward the user with virtual lottery tickets for a daily check-in to the mobile application.

6. The system according to claim 5, wherein the system is configured to determine when a user has completed daily check-ins for consecutive days and rewards the user with additional virtual lottery tickets for achieving streaks of completed daily check-ins.

7. The system according to claim 1, wherein the system is configured to reward the user with virtual lottery tickets for reading health or insurance related articles provided through the mobile application and reward the user with additional virtual lottery tickets for achieving streaks of reading daily articles when the user has completed daily article readings for consecutive days.

8. The system of claim 1, wherein the virtual lottery tickets define at least three levels of tickets configured to increase a chance of winning in the raffle as the levels increase.

9. The system of claim 8, wherein the level of tickets include bronze tickets, silver tickets, gold tickets and optionally black tickets; wherein silver tickets increase the chances of winning in the raffle as compared to bronze tickets and gold tickets increase the chances of winning in the raffle as compared to silver tickets, wherein at least 5 bronze tickets can be converted into a silver ticket and at least 3 silver tickets can be converted into a gold ticket, and wherein the black tickets allow for entry into VIP raffles.

10. A system for a reward-based health program provided through a mobile application, comprising:
    (a) a mobile device having a visual user interface, a processor, a storage unit configured to store data, and a wireless communication module configured to wirelessly communicate;
    (b) a mobile application provided on the mobile device configured to communicate with a remote online community through the wireless communication module;
    (c) an activity monitoring device including one or more biometric sensors configured to detect and track physical activity data corresponding to activity performed by a user of the mobile application including step counts; and
    (d) a communication network accessible by the mobile application through the wireless communication module, wherein the communication network is configured to host a plurality of users tracking individual physical activity data;
    wherein the activity monitoring device is configured to transmit the physical activity data to the mobile device through the mobile application;
    wherein the mobile device is configured to communicate the physical activity data from the activity monitoring device to the mobile application and collect and store the data through the mobile application;

wherein the mobile application is configured to communicate the physical activity data to the communication network wherein the plurality of users within the communication network can view and monitor progress related to physical activity data of other users having individually tracked physical activity data, wherein the mobile application is configured to reward the user with virtual lottery tickets based on achieving daily goals associated with the physical activity, wherein the virtual lottery tickets are configured to be collected and applied by the user to enter raffles for prizes through the mobile application, wherein the visual user interface is configured to display the virtual lottery tickets, progress related to the goals, and physical activity data, and wherein the mobile application is configured to: (i) generate rewards with virtual lottery tickets for streaks associated with achieving the daily goals, (ii) determine a lost streak when a daily goal is not completed on that day, (iii) generate a streak-saver prompt on a next day following the day of the lost streak on the visual user interface to revive the lost streak; and (iv) generate a streak-saver health-related activity task on that next day upon completion of which revives and continues the streak as if the lost streak had not occurred.

11. The system according to claim 10, wherein the activity monitoring device is a wearable computing device including a pedometer configured to wirelessly communicate with the mobile device.

12. The system according to claim 10, wherein the activity monitoring device is incorporated in the mobile device and comprises a pedometer configured to measure steps taken by the user.

13. The system according to claim 10, wherein the mobile application is configured to generate daily goals in the form of a task related to physical activity and reward the user with virtual lottery tickets for completing daily goals.

14. The system according to claim 10, wherein the system is configured to reward the user with virtual lottery tickets for completing a daily check-in to the mobile application.

15. The system according to claim 14, wherein the system is configured to determine when a user has completed daily check-ins for consecutive days and rewards the user with additional virtual lottery tickets for achieving streaks of completed daily check-ins.

16. The system according to claim 10, wherein the system is configured to reward the user with virtual lottery tickets for reading health or insurance related articles provided through the mobile application and reward the user with additional virtual lottery tickets for achieving streaks of reading daily articles where the user has completed daily article readings for consecutive days.

17. The system of claim 10, wherein the virtual lottery tickets define at least three levels of tickets configured to increase a chance of winning in the raffle as the levels increase.

18. The system of claim 17, wherein the level of tickets include bronze tickets, silver tickets, gold tickets and optionally black tickets; wherein silver tickets increase the chances of winning in the raffle as compared to bronze tickets and gold tickets increase the chances of winning in the raffle as compared to silver tickets, wherein at least 5 bronze tickets can be converted into a silver ticket and at least 3 silver tickets can be converted into a gold ticket, and wherein the optional black tickets allow for entry into VIP raffles.

19. A method of rewarding a health-related activity through a mobile application, the method comprising:

(a) providing a mobile application on a mobile device associated with a user, the mobile device having a visual user interface for displaying progress, a processor, a storage unit configured to store data, and a wireless communication module configured to wirelessly communicate;

(b) tracking and collecting physical activity data of the user through an activity monitoring device;

(c) communicating the physical activity data to the mobile application; and (d) rewarding the user with virtual lottery tickets based on satisfying preset criteria generated through the mobile application as daily physical activity goals, wherein the virtual lottery tickets are configured to be used by the user to enter raffles for prizes through the mobile application;

(e) rewarding lottery tickets for completing physical activity goals, checking-in to into the mobile application for consecutive days, or completing health-related tasks including reading health articles provided in the mobile application;

wherein the mobile application is configured to: (i) generate rewards with virtual lottery tickets for streaks associated with achieving the daily goals, (ii) determine a lost streak when a daily goal is not completed on that day, (iii) generate a streak-saver prompt on a next day following the day of the lost streak on the visual user interface to revive the lost streak; and (iv) generate a streak-saver health-related activity task on that next day upon completion of which revives and continues the streak as if the lost streak had not occurred.

20. The method of claim 19, wherein the virtual lottery tickets define at least three levels of tickets configured to increase a chance of winning in the raffle as the levels increase.

* * * * *